US007689287B2

(12) United States Patent
Han

(10) Patent No.: US 7,689,287 B2
(45) Date of Patent: Mar. 30, 2010

(54) METHOD OF AIDING SMOKING CESSATION

(75) Inventor: Ji Sheng Han, Beijing (CN)

(73) Assignee: Moleac Pte. Ltd., Singapore (SG)

( * ) Notice: Subject to any disclaimer, the term of this patent is extended or adjusted under 35 U.S.C. 154(b) by 1127 days.

(21) Appl. No.: 11/244,011

(22) Filed: Oct. 4, 2005

(65) Prior Publication Data

US 2006/0085050 A1 Apr. 20, 2006

Related U.S. Application Data

(60) Provisional application No. 60/617,477, filed on Oct. 7, 2004.

(51) Int. Cl.
*A61N 1/32* (2006.01)
*A61H 39/00* (2006.01)

(52) U.S. Cl. .......................................... 607/58; 607/69

(58) Field of Classification Search .................. 607/58, 607/1-3, 45, 46, 66-74; 600/547-548
See application file for complete search history.

(56) References Cited

U.S. PATENT DOCUMENTS

| | | | | |
|---|---|---|---|---|
| 4,646,744 | A * | 3/1987 | Capel | 607/58 |
| 5,269,304 | A * | 12/1993 | Matthews | 607/46 |
| 5,417,706 | A | 5/1995 | Chun | |
| 5,601,598 | A | 2/1997 | Fisher | |
| 5,643,173 | A * | 7/1997 | Welles | 600/26 |
| 5,950,635 | A | 9/1999 | Garcia-Rill et al. | |
| 5,957,951 | A | 9/1999 | Cazaux et al. | |
| 6,237,603 | B1 | 5/2001 | Mendell | |
| 6,267,721 | B1 * | 7/2001 | Welles | 600/26 |
| 2002/0156501 | A1 | 10/2002 | Grey et al. | |
| 2003/0083720 | A1 * | 5/2003 | Peterson et al. | 607/88 |
| 2004/0088036 | A1 | 5/2004 | Gilbert | |
| 2004/0102819 | A1 * | 5/2004 | Zou et al. | 607/46 |

FOREIGN PATENT DOCUMENTS

| | | |
|---|---|---|
| AU | 611745 | 6/1991 |
| CN | 1101583 A1 | 4/1995 |
| CN | 1140062 A | 1/1997 |

OTHER PUBLICATIONS

Ausfeld-Hafter B, Marti F, Hoffmann S. Smoking cessation with ear acupuncture. Descriptive study on subjects after a smoking cessation treatment with ear acupuncture. Forschende Komplementarmedizin und Klassische Naturheilkunde 2004;11(1):8-13.

(Continued)

*Primary Examiner*—Carl H Layno
*Assistant Examiner*—Jessica Sarcione
(74) *Attorney, Agent, or Firm*—Wells St. John P.S.

(57) ABSTRACT

Methods which are useful to aid in smoking cessation. The methods generally comprise applying an electrical current to the subject in the vicinity of two or more acupuncture points selected from acupuncture points in or on the arms and hands of the subject. Suitable points include the Hegu acupuncture point (LI-4), a point on the opposite side of the hand to the Hegu acupuncture point, the Wai guan acupuncture point (SJ-5), and the Nei guan acupuncture point (PC-6).

26 Claims, 5 Drawing Sheets

OTHER PUBLICATIONS

Bier I.D, Wilson J, Studt P, Shakleton M. Auricular acupuncture, education, and smoking cessation: a randomized, sham-controlled trial. American Journal of Public Health 2002;92(10):1642-7.
Borchgrevink C.F. Research in alternative medicine. What is documented, and what is documentation? Tidsskrift for Den Norske Laegeforening 1997;117(17):2469-73.
Clavel-Chapelon F, Paoletti C, Benhamou S. A randomized 2×2 factorial design to evaluate different smoking cessation methods. Revue d Epidemiologie et de Sante Publique 1992;40(3):187-90.
Clavel-Chapelon F, Paoletti C, Benhamou S. Smoking cessation rates 4 years after treatment by nicotine gum and acupuncture. Preventive Medicine 1997;26(1):25-8.
Cottraux J, Schbath J, Messy P, Mollard E, Juenet C, Collet L. Predictive value of MMPI scales on smoking cessation programs outcomes. Acta Psychiatrica Belgica 1986:86(4):463-9.
Cox L.S., Tiffany S.T, Christen A.G. Evaluation of the brief questionnaire of smoking urges (QSU-brief) in laboratory and clinical settings. Nicotine Tob Res. Feb. 2001;3(1):3-6.
Ernst E. Acupuncture-how effective is it really? Fortschritte der Medizin 1998;116(1-2):20-6.
Fuller J.A. Smoking withdrawal and acupuncture. Medical Journal of Australia 1982:1(1):28-9, 1982.
Garrison M.M, Christakis D.A, Ebel B.E, Wiehe S.E, Rivara F.P. Smoking cessation interventions for adolescents: a systematic review. American Journal of Preventive Medicine 2003;25(4):363-7.
Grau A.I., Prous J.R. Nicotine Addiction—Executive Summary. Drugs Today (Barc), Jun. 2005;41(6):419-25.
Haustein K.O. Institute for Nicotine Research and Smoking Cessation, Erfurt, Germany. Pharmacotherapy of nicotine dependence. International Journal of Clinical Pharmacology & Therapeutics 2000;38(6):273-90.
He D, Berg J.E, Hostmark A.T. Effects of Acupuncture on Smoking Cessation or Reduction for Motivated Smokers. Preventive Medicine 1997;26:208-214.
He D, Medbo J.I, Hostmark AT. Effect of acupuncture on smoking cessation or reduction: an 8-month and 5-year follow-up study. Preventive Medicine 2001;33(5):364-72.
Kelley M.J and McCrory D.C Prevention of lung cancer: summary of published evidence. Chest 2003;123(1 Suppl):50S-59S.
Lando H.A. Smoking cessation products and programs. Alaska Medicine 1996;38(2):65-68.
Law M. and Tang J.L. An analysis of the effectiveness of interventions intended to help people stop smoking. Archives of Internal Medicine 1995;155(18):1933-41.
Linde K, Vickers A, Hondras M, Ter Riet G, Thormahlen J, Berman B, Melchart D. Systematic reviews of complementary therapies—an annotated bibliography. Part 1: acupuncture. BMC Complementary & Alternative Medicine 2001;1(1):3.
Margolin A, Avants S.K, Holford T.R. Interpreting conflicting findings from clinical trials of auricular acupuncture for cocaine addiction: does treatment context influence outcome? Journal of Alternative & Complementary Medicine 2002;8(2):111-21.
Mohit A. A brief overview of Drug Abuse and Guiding principles for building programs for reducing demand and harm related to the above of drug. The First Consultation of Regional Advisory Panel on the Impact of Drug Abuse (RAPID) Cairo, Egypt, Sep. 23-26, 2002.
Tiffany S.T., Drobes D.J. The development and initial validation of a questionnaire on smoking urges. British Journal of Addiction Nov. 1991;86(11):1467-76.
Waite N.R and Clough J.B. A single -blind, placebo-controlled trial of a simple acupuncture treatment in the cessation of smoking. British Journal of General Practice 1998;48(433):1487-90.
White A.R, Resch K.L, Ernst E. Randomized trial of acupuncture for nicotine withdrawal symptoms. Archives of Internal Medicine 1998;158(20)2251-5.
White A.R, Resch K.L, Ernst E. A meta-analysis of acupuncture techniques for smoking cessation. Tobacco Control 1999;8(4):393-7.
White A.R, Rampes H, Ernst E. Acupuncture for smoking cessation. [update of Cochrane Database Syst Rev. 2000;(2):CD000009.] Cochrane Database of Systematic Reviews 2002;(2):CD000009.
Willemsen M.C, Wagena E.J, van Schayck C.P. The efficacy of smoking cessation methods available in the Netherlands: a systematic review based on Cochrane data. Nederlands Tijdschrift voor Geneeskunde 2003;147 (19):922-7.
Yiming C, Changxin Z, Ung W.S, Lei Z, Kean L.S. Laser acupuncture for adolescent smokers—a randomized double-blind controlled trial. American Journal of Chinese Medicine 2000;28(3-4):443-9.

* cited by examiner

METHOD OF AIDING SMOKING CESSATION

RELATED PATENT DATA

This application claims priority to U.S. Provisional Application Ser. No. 60/617,477, which was filed Oct. 7, 2004.

FIELD OF THE INVENTION

The invention relates to a method of aiding smoking cessation. More particularly the inventions relates to a method of aiding smoking cessation by application of electrical current to acupuncture points.

BACKGROUND TO THE INVENTION

Acupuncture originated in ancient China approximately 4000 years ago. It is based upon metaphysical concepts of "ch'i" (Qi), a supposed body energy that runs through hypothesized channels called "meridians." On these "meridians" are 365 designated acupuncture points that can be used for stimulation to balance "yin and yang" by relieving blockages in the flow of "ch'i."

The physiological and anatomical basis of acupuncture points has been investigated. Acupuncture points have been found to be located in the vicinity of the small or large peripheral nerves and their bifurcations, motor points of neuromuscular attachments, blood vessels, ligaments and suture lines of the skull. A double-blind, placebo-controlled randomized study reported that true acupuncture points have higher local temperature and lower electrical resistance, compared to non-acupuncture points.

The use of auricular (ear) acupuncture as a method to aid smokers to overcome their addiction and/or overcome nicotine dependency has been previously reported. Many conflicting results have been reported with a number of recent publications such as Kelly and McCrory (2003), Willemsen et al. (2003), White A. R et al. (2002), Linde et al. (2001), Haustein K. O (2000), White A. R (1999), White A. R et al. (1998), Borchgrevink C. F (1997), Clavel-Chapelon F et al. (1997), Lando H. A (1996), Law and Tang (1995) and Clavel-Chapelon F et al. (1992) reporting that acupuncture is not effective in helping promote smoking cessation or helping to overcome nicotine dependency. Alternatively other authors such as Ausfeld-Hafter B et al. (2004), Bier I. D et al. (2002), He D et al. (2001), Yiming C et al. (2000), Waite Clough (1998), Cottraux J et al. (1986) and Fuller J. A (1982) have reported that auricular acupuncture is a viable method for helping promote smoking cessation.

This inconsistency has been highlighted by researches such as Garrison M. M et al. (2003), Margolin A et al (2002) and Ernst E (1998), and the need for clarification has been stated.

Furthermore, the existence of specific anti-smoking acupuncture points has been questioned since some studies show little difference in cessation rates between "real" and "sham" acupuncture groups.

While non-ear acupuncture points have previously been used to examine the efficacy of acupuncture for promoting smoking cessation, their use has been part of a general combination treatment strategy. For example, He D et al. (1997) found that a combination of body acupuncture (Lieque and Kongzui), ear acupuncture (Shenmen, mouth, lung), as well as acupressure (Shenmen, mouth, lung, trachea, hunger, endocrine) is effective in promoting smoking cessation.

A number of devices that aid smokers to quit smoking have been described. Australian Patent AU611745 describes a combined sound-generating device and auricle electrical acupuncture device for assisting addiction treatment. The device is made of a clip electrode and buzzer that is attached to the ear to deliver a high voltage stimulus of low current and ultra-low frequency sound.

The use of a removable attachable wrist band to help an addicted cigarette smoker permanently quit smoking has been suggested in U.S. Pat. No. 5,601,598. As described, the wrist band is placed on a user's wrist such that the acupressure stimulator is positioned proximal to the L-7 acupuncture point so that snapping of the band against the wrist stimulates the acupuncture point. The authors suggest that the wrist band has a dual function of both providing a non-aversive behavioural modification as well as stimulating the L-7 acupuncture point.

Chinese patent application CN1140062 describes the use of a plaster comprising ingredients such as clove, cinnamon bark, areca and ichthyol that is applied to the Lieque acupuncture point to assist people to give up smoking. The authors suggest that the plaster works by irritating the sense organ in the oral cavity, resulting in a tingling in the tip of tongue and causing the taste of tobacco to become bitter.

It is an object of the present invention to provide an improved or alternative method of aiding smoking cessation or to at least provide the public with a useful choice.

Other objects of the invention may become apparent from the following description which is given by way of example only.

SUMMARY OF THE INVENTION

According to a first aspect of the invention there is provided a method of reducing the desire to smoke in a subject in need thereof comprising applying an electrical current to the subject in the vicinity of two or more acupuncture points selected from acupuncture points in or on the arms and hands of the subject.

According to a further aspect of the invention there is provided a method of aiding smoking cessation in a subject in need thereof comprising applying an electrical current to the subject in the vicinity of two or more acupuncture points selected from acupuncture points in or on the arms and hands of the subject.

According to a further aspect of the invention there is provided a method of alleviating the symptoms of nicotine withdrawal in a subject in need thereof comprising applying an electrical current to the subject in the vicinity of two or more acupuncture points selected from acupuncture points in or on the arms and hands of the subject.

According to a further aspect of the invention there is provided a method of alleviating the symptoms of craving resulting from nicotine addiction in a subject in need thereof comprising applying an electrical current to the subject in the vicinity of two or more acupuncture points selected from acupuncture points in or on the arms and hands of the subject.

According to a further aspect of the invention there is provided a method of reducing or alleviating nicotine craving in a subject in need thereof comprising applying an electrical current to the subject in the vicinity of two or more acupuncture points selected from acupuncture points in or on the arms and hands of the subject.

According to a further aspect of the invention there is provided a method of treating nicotine addiction in a subject in need thereof comprising applying an electrical current to the subject in the vicinity of two or more acupuncture points selected from acupuncture points in or on the arms and hands of the subject.

In one embodiment the acupuncture points are selected from:

the Hegu (LI-4) acupuncture point, a point on the opposite side of the hand to the Hegu acupuncture point, the Nei guan (PC-6) acupuncture point, and the Wai guan (SJ-5) acupuncture point.

Preferably electrical current is applied in the vicinity of 2, 3 or 4 of these acupuncture points, preferably 2 or 4 of these acupuncture points.

In one embodiment the electrical current is applied through at least one electrode placed substantially in or on the subject in the vicinity of a selected acupuncture point.

Preferably the electrode is selected from a needle electrode and a skin contact electrode.

Preferably electrical current is applied in the vicinity of a selected acupuncture point using a single needle electrode or two skin contact electrodes.

Preferably electrical current is applied in the vicinity of a selected acupuncture point by inserting a single needle electrode into the subject in the vicinity of the selected acupuncture point.

Preferably electrical current is applied in the vicinity of a selected acupuncture point by placing a first skin contact electrode on a first skin surface adjacent the selected acupuncture point and a second skin contact electrode on a second skin surface adjacent the selected acupuncture point. Preferably the first and second skin surfaces are on opposite sides of a limb in which the selected acupuncture point is located.

In one embodiment the electrical current is applied at or within about 1 to 2 cm, more preferably within about 0.5, 0.6, 0.7, 0.8, or 0.9 cm of the acupuncture point.

Preferably the electrical current is applied at or within about 1 to 2 cm, more preferably within about 0.5, 0.6, 0.7, 0.8, or 0.9 cm of the Hegu (LI-4) acupuncture point.

Preferably the electrical current is applied at or within about 1 to 2 cm, more preferably within about 0.5, 0.6, 0.7, 0.8, or 0.9 cm of a point on the opposite side of the hand to the Hegu acupuncture point.

Preferably the electrical current is applied at or within about 1 to 2 cm, more preferably within about 0.5, 0.6, 0.7, 0.8, or 0.9 cm of the Nei guan (PC-6) acupuncture point.

Preferably the electrical current is applied at or within about 1 to 2 cm, more preferably within about 0.5, 0.6, 0.7, 0.8, or 0.9 cm of the Wai guan (SJ-5) acupuncture point.

In one embodiment the current is at or is greater than the threshold of the subject. Preferably the current is at least about twice the threshold of the subject.

Preferably the current is at least about 1, 2, 4, 6, 8, 10, 12, 14, 16, 18, 20, 22 or 24 mA.

Preferably the current is about 4 to about 16 mA.

In one embodiment the current is applied at a frequency of at least about 1 Hz. Preferably the current is applied at a frequency of less than about 120 Hz. Preferably the current is applied at a frequency of about 2 Hz to about 100 Hz.

In one embodiment the current is alternated between at least two frequencies. Preferably the frequency of the current is alternated from a frequency of about 1, 2, 3, 4, 5, 6, 7, 8, 9, or 10 Hz to a frequency of about 15, 30, 40, 50, 60, 70, 80, 90, 100, 110 or 120 Hz.

In one embodiment the frequency is alternated every 1, 2, 3, 4 or 5 seconds. Preferably the frequency is alternated every 3 seconds.

Most preferably the frequency is alternated from a frequency of about 2 Hz to a frequency of about 100 Hz every 3 seconds.

In one embodiment the frequency is alternated from a frequency of about 2 Hz to a frequency of about 15 Hz every 3 seconds.

In one embodiment the electrode receives an electrical current from an electro-acupuncture device.

In an embodiment where more than one electrode is used, preferably electrical current is applied to each electrode simultaneously.

In one embodiment the electro-acupuncture device has at least a first channel and a second channel which can independently provide an electrical current.

In one embodiment each channel is connected to at least one electrode, preferably multiple electrodes, and more preferably each channel is connected to two electrodes.

In one embodiment the first channels provides a first set of conditions and the second channel provides a second set of conditions.

In one embodiment the method is carried out according to a regime comprising:

(1) an initial period, and (2) a weaning period.

In one embodiment the initial period is between about two to about eight weeks in duration. Most preferably said initial period is about four weeks in duration.

Preferably the method of the invention is carried out two, three, four or five times daily during the initial period, more preferably three or four times daily.

Preferably the method of the invention is carried out in the morning, after lunch, in the mid afternoon, and before sleeping.

In one embodiment the weaning period is about two to about 12 weeks in duration and the method of the invention is carried out about one or two times daily or whenever craving occurs.

Other aspects of the invention may become apparent from the following description which is given by way of example only and with reference to the accompanying drawings.

This invention may also be the broadly to consist in the parts, elements and features referred to or indicated in the specification of the application, individually or collectively, and any or all combinations of any two or more of the parts, elements or features, and where specific integers are mentioned herein which have known equivalents in the art to which this invention relates, such known equivalents are deemed to be incorporated herein as if individually set forth.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7).

BRIEF DESCRIPTION OF THE DRAWINGS

The invention will now be described by way of example only and with reference to the drawings in which.

DETAILED DESCRIPTION OF THE INVENTION

Figure 1:
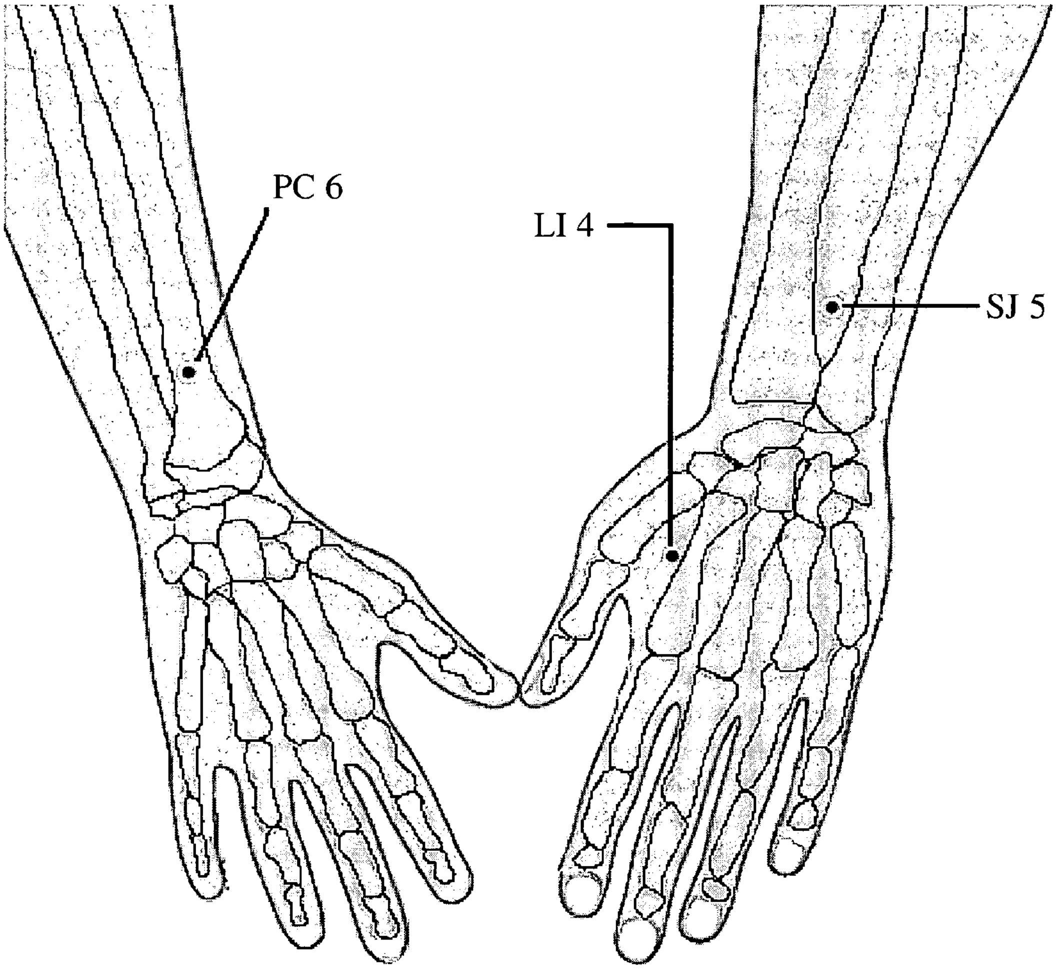
FIG. 1 illustrates the positioning of preferred acupuncture points on the human forearm.

The present invention provides methods which are useful to reduce the desire to smoke, aid in smoking cessation, alleviate the symptoms of nicotine withdrawal, alleviate the symptoms of craving resulting from nicotine addiction, alleviate nicotine craving, or treat nicotine addiction depending on the needs of a subject employing the method.

The World Health Organization (WHO) classifies smoking and nicotine addiction as one of the most prevalent addictive human behaviour worldwide. In spite of increased awareness and public action, it remains the leading cause of preventable disease and death. According to WHO, there are nearly five million deaths per year that results from diseases triggered by tobacco addiction behaviour (Grau et al, 2005).

Successful smoking cessation requires changing the behavioural pattern of the individual (Mohit, A., 2002). The current invention focuses on assisting the individual to change his behaviour towards smoking.

The method of the invention generally comprises applying an electrical current to the subject in the vicinity of two or more acupuncture points selected from acupuncture points in or on the arms and hands of the subject. This technique is known as electro-acupuncture.

Electro-acupuncture consists of exposing subjects to electrical stimulations delivered either through metal needles inserted into tissue or through the use of self-adhesive skin electrodes.

While many electro-acupuncture devices are known in the art, any device able to stimulate desired acupuncture points could be used. A suitable device may employ electrodes including acupuncture needles or skin contact electrodes attached to an electrical source.

Such electrodes may be placed in the vicinity of acupuncture points of interest separately or simultaneously. In addition, the electrodes may be employed in an article that is designed to be worn over the acupuncture points of interest in the form of a removable glove, sleeve, bracelet or watch-like device. Such devices would provide an advantage of being portable allowing self-administration by the subject.

While the devices recited above rely on physical stimulation of the acupuncture points it may be possible to use non-invasive techniques to provide the stimulation that do not rely on direct physical proximity. For example, we envisage that it may be possible to use a device which envelopes the hand and delivers the stimulation without actually physical touching the hand. Such a device may employ an electrical field, laser acupuncture or the like.

The method of the invention comprises applying an electrical current to a subject need thereof in the vicinity of two or more acupuncture points selected from:

- the Hegu acupuncture point (LI-4) which is located on the back of each hand where the bones of the thumb and index finger meet;
- a point on the opposite side of the hand to the Hegu acupuncture point;
- the Wai guan acupuncture point (SJ-5) which is located 2 cun above the transverse crease of dorsum of wrist between the radius and the ulna; and
- the Nei guan acupuncture point (PC-6) which is point located 2 cun above the transverse crease of the wrist, between the tendons of m. palmaris longus and m. flexor radialis.

As used herein, the term "cun" is intended to mean a unit of distance based on the width of a person's finger so that 1 cun is approximately equal to the distance across the dorsal surface of the middle finger at the proximal interphalangeal joint.

FIG. 1 illustrates the location of these four acupuncture points: Hegu (LI-4) (both upper and lower side of the hand), Wai guan (SJ-5), and Nei guan (PC-6) acupuncture points.

Preferably electrical current is applied in the vicinity of 2, 3 or 4 of these acupuncture points, preferably 2 or 4 of these acupuncture points.

In one embodiment the electrical current is applied through at least one electrode placed substantially in or on the subject in the vicinity of a selected acupuncture point.

Preferably the electrode is selected from a needle electrode and a skin contact electrode.

Preferably electrical current is applied in the vicinity of a selected acupuncture point using a single needle electrode or two skin contact electrodes.

Preferably electrical current is applied in the vicinity of a selected acupuncture point by inserting a single needle electrode into the subject in the vicinity of the selected acupuncture point. The needle is inserted through the skin of the subject into the tissue of the subject's arm or hand until a portion of the needle is in the desired location within the vicinity of the selected acupuncture point.

Preferably electrical current is applied in the vicinity of a selected acupuncture point by placing a first skin contact electrode on a first skin surface adjacent the selected acupuncture point and a second skin contact electrode on a second skin surface adjacent the selected acupuncture point. Preferably the first and second skin surfaces are on opposite sides of a limb in which the selected acupuncture point is located. The use of at least two skin contact electrodes in this way so that the electrical current passes through the acupuncture point located below the skin surface may ensure current is applied in the vicinity of the selected acupuncture point at a useful level.

Preferably the electrical current is applied in the vicinity of a selected acupuncture point to stimulate one or more of the selected acupuncture point, a nerve, subcutaneous tissue, muscle fibres and a biological system in the vicinity of the selected acupuncture point.

Without wishing to be bound by theory, the efficacy of the method of the invention is thought to derive from the ability of the method to stimulate the selected acupuncture point or a physical structure in the vicinity of the selected acupuncture point. Possible physical structures include one or more of a nerve, subcutaneous tissue, muscle fibre and a biological system.

The term "biological system" as used herein is intended to refer to a signalling or regulatory network, either chemical or electrical, that may be stimulated by the method of the invention. Such networks include the central nervous system, peripheral nervous system, hormonal regulatory systems and chemical signalling pathways.

Stimulating the acupuncture point itself or a physical structure in the vicinity of the selected acupuncture point has been shown to trigger the synthesis and the release of human natural molecules. These natural molecules can act directly on a number of body's self regulation systems, or trigger through biological pathways the modulation of other molecules that will act remotely from the stimulation point on the body homeostasis, including stimulating the body's natural healing abilities and promoting physical and emotional well-being. As an illustration, acupuncture performed remotely has been documented to affect the parts of the central nervous system related to sensation and involuntary body functions, such as immune reactions and processes whereby a person's blood pressure, blood flow, and body temperature are regulated.

In one embodiment the electrical current is applied at or within about 1, 2, 3, 4 or 5 cm, preferably about 1 to 2 cm and more preferably within about 0.5, 0.6, 0.7, 0.8, or 0.9 cm of the acupuncture point.

In those embodiments where multiple electrodes are used, once each electrode is placed in the desired position in the vicinity of the selected acupuncture point, each electrode can be activated simultaneously to provide simultaneous stimulation of said acupuncture points.

In one embodiment the electrode receives an electrical current from an electro-acupuncture device. In one embodiment the electro-acupuncture device can deliver multiple sets of stimulatory conditions, said conditions defined by the strength, frequency, range, variance and duration of stimulation. The delivery of said multiple sets of conditions preferably occurs via separate channels.

In an embodiment where more than one electrode is used, preferably electrical current is applied to each electrode simultaneously. In one embodiment the electro-acupuncture device has at least a first channel and a second channel which can independently provide an electrical current. In one embodiment each channel is connected to at least one electrode, preferably multiple electrodes, and more preferably each channel is connected to two electrodes.

In one embodiment the first channels provides a first set of conditions and the second channel provides a second set of conditions.

When stimulating multiple acupuncture point simultaneously, the use of multiple channels delivering multiple sets of stimulatory conditions allows the user to choose which set of stimulatory conditions is most appropriate for any particular acupuncture point.

In a preferred embodiment skin contact electrodes are applied to four points as follows:

First channel: one electrode is placed on the Hegu acupuncture point (LI-4) and the other electrode is placed on the corresponding opposite point of the same hand (i.e. on the palm side).

Second channel: one electrode is placed on the Nei guan point (PC-6) and the other electrode is placed on the on Wei guan point (SJ-5).

Preferably the electrical current is applied at or within about 1, 2, 3, 4 or 5 cm and more preferably within about 0.5, 0.6, 0.7, 0.8, or 0.9 cm of the Hegu (LI-4) acupuncture point.

Preferably the electrical current is applied at or within about 1, 2, 3, 4 or 5 cm and more preferably within about 0.5, 0.6, 0.7, 0.8, or 0.9 cm of a point on the opposite side of the hand to the Hegu acupuncture point.

Preferably the electrical current is applied at or within about 1, 2, 3, 4 or 5 cm and more preferably within about 0.5, 0.6, 0.7, 0.8, or 0.9 cm of the Nei guan (PC-6) acupuncture point.

Preferably the electrical current is applied at or within about 1, 2, 3, 4 or 5 cm and more preferably within about 0.5, 0.6, 0.7, 0.8, or 0.9 cm of the Wai guan (SJ-5) acupuncture point.

A range of stimulation strengths can be used to obtain the desired results. We envisage that the lower limit of this range would be about 1 mA, or at least the subject's threshold. In addition, we envisage that the upper limit of this range would be three times the subject's threshold or 24 mA. A current intensity of 24 mA is typically the upper limit as stimulation above this may cause unpleasant muscle twitching or sensation. In the preferred embodiment of the present invention the strength of stimulation is approximately two to three times the subject's threshold. It should be appreciated that due to the variability of peoples' sensitivity to electrical current, the actual strength of stimulation used (i.e. the current in mA) is dependent on each subject's pain threshold. While a preferred range is about 4 to 16 mA, the preferred range of stimulation strength may need to be adjusted for each individual. For example, sensitivity to pain decreases with age so that a preferred range for an older subject may need to be adjusted to a higher range (e.g. 3 to 7, 4 to 8, 5 to 9, 6 to 10, 5 to 12 mA etc). A preferred range for a younger subject may be 1 to 3, 2 to 4 or 3 to 5 mA for example.

Due to this variability in pain threshold it will usually be necessary to test a patent's threshold to the electrical stimulation. This is typically done by stimulating the subject with very low current strength (less than 1 mA) and then increasing the strength until the subject first notices the electrical stimulation. The point at which the subject first notices the electrical stimulation is the subject's threshold.

In one embodiment the current is at or is greater than the threshold of the subject. Preferably the current is at least about twice the threshold of the subject.

Preferably the current is at least about 1, 2, 4, 5, 6, 8, 10, 12, 14, 16, 18, 20, 22 or 24 mA.

In the preferred embodiment of the present invention, the electro-acupuncture is used with alternating current, although direct current can also be used.

Figure 2:
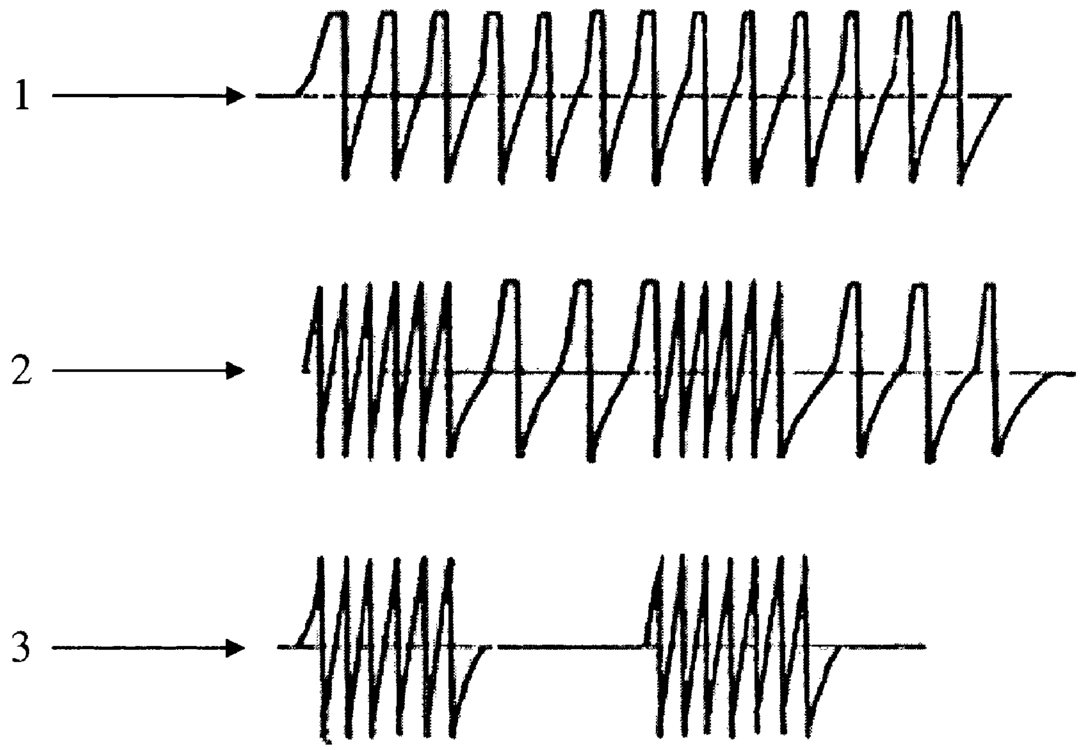
FIG. 2 is a diagram illustrating the samples of different wave forms produced by electro-acupuncture devices.

With reference to FIG. 2, a continuous wave form 1, a sparse and dense wave form 2 or an intermittent wave 3 are examples of different types of wave forms that can be produced by an electro-acupuncture device. A continuous wave is preferred. The overall frequency of stimulus (either by continuous wave or pulses of dense waves) is preferably set similar to the frequency of nerve impulses induced by manual stimulation via twirling or lifting/thrusting of an acupuncture needle.

A range of stimulation frequencies can be used to obtain the desired results. We envisage that the lower limit of this range would be about 1 Hz with an upper limit of about 120 Hz and more a preferred range of about 2 to about 100 Hz. Thus, in one embodiment the current is applied at a frequency of at least about 1 Hz. Preferably the current is applied at a frequency of less than about 120 Hz. A suitable frequency for a given subject may be determined by a skilled worker with regard to the effectiveness of a chosen frequency over time when employed in a method of the invention.

In a preferred embodiment of the present invention the frequency of stimulation is alternated between multiple frequencies. Preferably the frequency of stimulation is alternated between about 2 and 100 Hz, although it should be recognised that a range of frequencies above and below this could be used depending on individual patent variance (e.g. a lower value of about 1, 2, 3, 4, 5, 6, 7, 8, 9, or 10 Hz and an upper value of about 15, 30, 40, 50, 60, 70, 80, 90, 100, 110 or 120 Hz etc).

In one embodiment the current is alternated between at least two frequencies. Preferably the frequency of the current is alternated from a frequency of about 2 Hz to a frequency of about 100 Hz.

Most preferably the frequency is alternated from a frequency of about 2 Hz to a frequency of about 100 Hz every 3 seconds.

In one embodiment the frequency is alternated from a frequency of about 2 Hz to a frequency of about 15 Hz every 15 seconds.

When applying the stimulation at multiple frequencies, current is used at each frequency for about 0.1 to about 30 seconds. Preferably each frequency is used for about 1 to 6 seconds and more preferably for about 3 seconds. Thus, in one embodiment the frequency is alternated every 1, 2, 3, 4 or 5 seconds. Preferably the frequency is alternated every 3 seconds.

In one preferred embodiment, the frequency is alternated from a frequency of about 2 Hz to a frequency of about 100 Hz every 3 seconds.

Stimulation of different acupuncture points may be conducted at different currents and frequencies. Where multiple frequencies are employed the period after which the frequency alternates may differ from point to point.

During the stimulation period, the subject may become adapted to the stimulus (this may typically happen after the first minute or two), with a gradual decline in response. The electrical output may then be adjusted in frequency and/or intensity to resume the sensation.

The strength and duration of stimulation to achieve maximum efficacy should be chosen to maintain patient comfort. The duration of standard electro-acupuncture is dependent on the subject's tolerance of the conditions used and their efficacy. Due to the variable response to the selected conditions between subjects, a successful session may be of any duration from a single application or as long as tolerable. Preferably each session usually lasts at least 1 minute, preferably 10 to 60 minutes, more preferably 10, 15, 20, 25, 30, 35 or 40 minutes and most preferably 20, 25 or 30 minutes.

Figure 3:
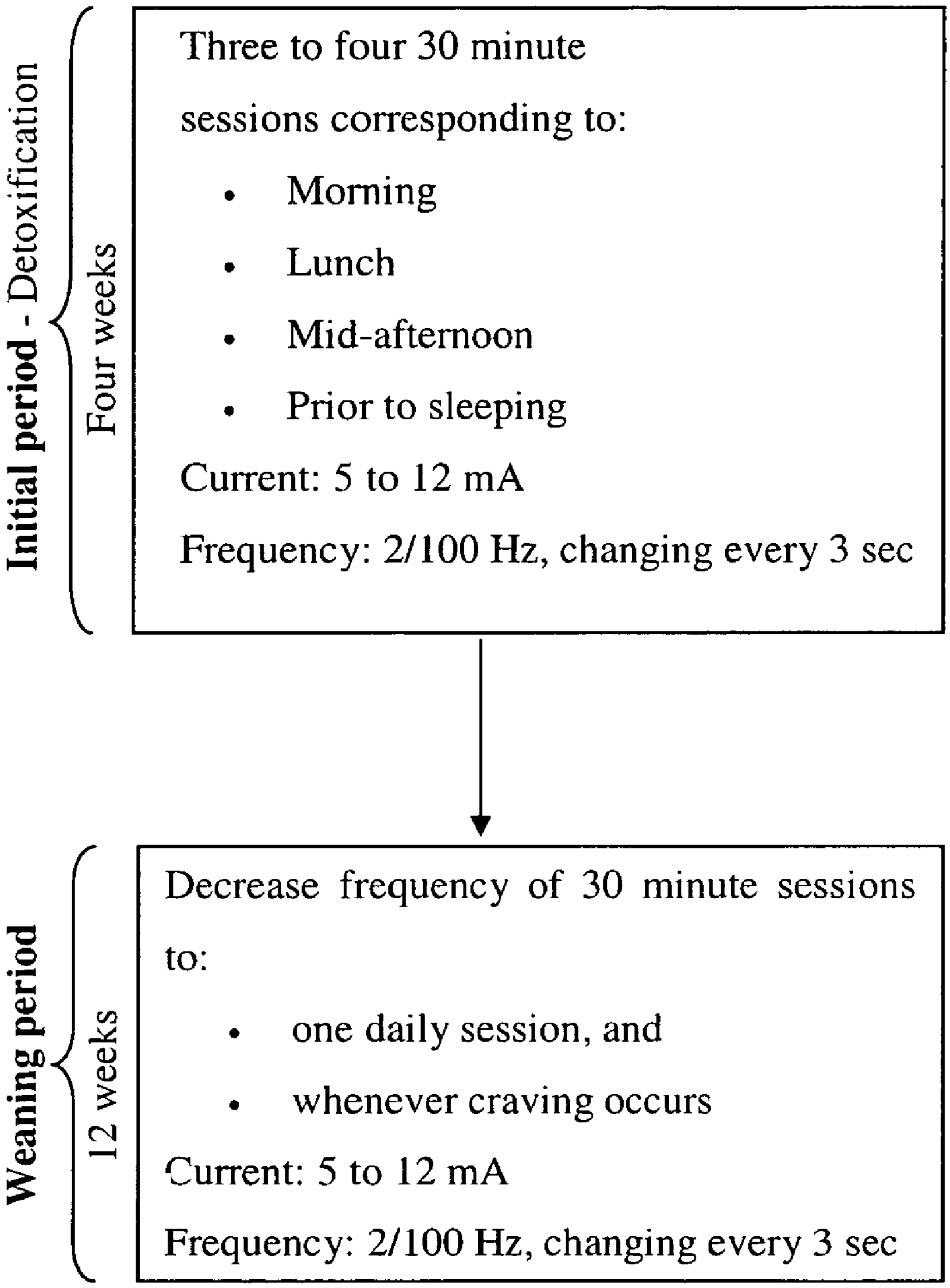
FIG. 3 is a flow chart illustrating a preferred regime for employing the method of the invention.

Referring to FIG. 3, in our preferred embodiment the method of the invention is employed differently in two stages. The initial stage is the detoxification phase which can be for a duration of between about two to about eight weeks, or as long as necessary to achieve substantial detoxification. In our preferred embodiment the detoxification stage lasts about four weeks with three to four sessions of acupuncture used daily, corresponding to a session in the morning, during or after lunch, during the mid-afternoon and prior to sleeping.

The second "weaning" stage entails the frequency of the sessions to decrease over a further period of time, eg 1, 2, 4, 6, 8, 10 or 12 weeks, or as long as necessary to achieve a substantial reduction in the frequency of craving. In our preferred embodiment the detoxifications stage lasts about two to about 12 weeks. An eventual aim may be to decrease the frequency of sessions to one session daily before sleeping and whenever craving occurs.

Thus, one embodiment the method is carried out according to a regime comprising:

a) an initial period, and b) a weaning period.

In one embodiment the initial period is about four weeks in duration and the method of the invention is carried out two, three, four or five times daily. In one embodiment the weaning period is about 12 weeks in duration and the method of the invention is carried out about one or two times daily or whenever craving occurs.

It should be appreciated by anyone skilled in the art that a session can be applied at any time in the eventuality that craving reoccurs. It should also be apparent that the length of the two stages, and the frequency of acupuncture sessions, can be varied to suit the needs of the person receiving the acupuncture.

EXPERIMENTAL

Experiment One

Three individual smokers used the method of the invention and reported a reduced craving sensation. The three individuals employed a session before sleeping and a half-session during the day. Each session was for 30 min in duration and comprised a current of twice the individuals threshold which cycled from 2 to 100 Hz every 3 seconds. An electro-acupuncture device was used which comprised two channels with each channel connected to two electrodes. This enabled simultaneous stimulation of each of the following acupuncture points:

the Hegu (LI-4) acupuncture point, a point on the opposite side of the hand to the Hegu acupuncture point, the Nei guan (PC-6) acupuncture point, and the Wai guan (SJ-5) acupuncture point.

Experiment Two

Study Design

We designed a double-blind comparative 1-day pilot study using the method of the invention, comparing two groups of 20 dependent smokers randomly assigned to:

A first group at 10 mA 'standard strength'; or

A second group at 5 mA 'lower strength'.

Upon arrival, all the subjects were asked to stop smoking for the overall study duration. To ensure subject compliance, three blood samples were taken to monitor cotinine concentration and six measurements were taken of carbon monoxide (CO) concentration in exhaled breath over the course of the study. A total amount of 20 to 30 mL of blood was taken during the course of the study.

Participation in the study lasted 26 hours (from Friday 6 pm to Saturday 8 pm) but subjects were allowed to go home from Friday 9 pm to Saturday 8.30 am.

In each group, subjects received four sessions of 30 minutes in duration that comprised a current that cycled from 2 to 100 Hz every three seconds. Each session was administered as follows:

1 session the first day at 6 pm 3 sessions on the second day at 8 am, 12 pm, and 4 pm.

The acupuncture device and the acupuncture points stimulated were the same as for Experiment One.

The primary efficacy outcome measure to assess the efficacy of the method of the invention was a standard questionnaire used for craving assessment: Questionnaire for Smoking Urge (QSU-brief), the second efficacy outcome measure was the VAS scale (Visual Analog Scale) for assessing craving for smoking.

Studies from Cox et al (2001) have clearly established the reliability of the QSU-Brief questionnaire within a controlled laboratory setting and an outpatient smoking cessation clinic and demonstrated that this measure was able to capture multidimensional features of self-reported craving. This questionnaire is a brief 10-item version of the QSU developed by Tiffany & Drobes (1991) to provide a more reliable measure and to assess the potential multidimensional nature of craving. Subjects were instructed to evaluate each of the 10 statements using a 7-point scale ranging from 'strongly disagree' to 'strongly agree'. Overall score was expressed as the average of the 10-item scores. Each item represents one of four distinct conceptualizations of smoking urges: desire to smoke, intent to smoke, anticipation of positive outcome, and anticipation of relief from withdrawal or negative effect. The 10 statements evaluated were:

1. I have a desire for a cigarette right now
2. Nothing would be better than smoking a cigarette right now
3. If it were possible, I probably would smoke now
4. I could control things better right now if I could smoke
5. All I want right now is a cigarette
6. I have an urge for a cigarette
7. A cigarette would taste good now
8. I would do almost anything for a cigarette now
9. Smoking would make me less depressed
10. I am going to smoke as soon as possible Study Procedure Day 1—6 pm
- Randomization to 5 mA or 10 mA group
- Smoke last cigarette for the following 26 hours
- Collection of blood samples for cotinine dosage
- Breathe into an apparatus used to collect and measure the CO in exhaled breath
- Complete the QSU-Brief Questionnaire and Visual Analogue Scale (VAS)
- Physical examination by a Medical Doctor
- First electro-acupuncture session (lasting 30 minutes)

Day 1—from 8 pm to 9 pm
- Complete the QSU-Brief Questionnaire and VAS
- Vital Signs control by a nurse Day 2—8 am
- Collection of blood samples for cotinine dosage
- Breathe into an apparatus used to collect and measure the CO in exhaled breath
- Complete the QSU-Brief Questionnaire and VAS
- Vital Signs control by a nurse
- Second electro-acupuncture session (lasting 30 minutes)

Day 2—12 am
- Breathe into an apparatus used to collect and measure the CO in exhaled breath
- Complete the QSU-Brief Questionnaire and VAS
- Vital Signs control by a nurse
- Third electro-acupuncture session (lasting 30 minutes)

Day 2—4 pm
- Collection of blood samples
- Breathe into an apparatus used to collect and measure the CO in exhaled breath
- Complete the QSU-Brief Questionnaire and VAS
- Vital Signs control by a nurse
- Fourth electro-acupuncture session (30 minutes)

Figure 4:
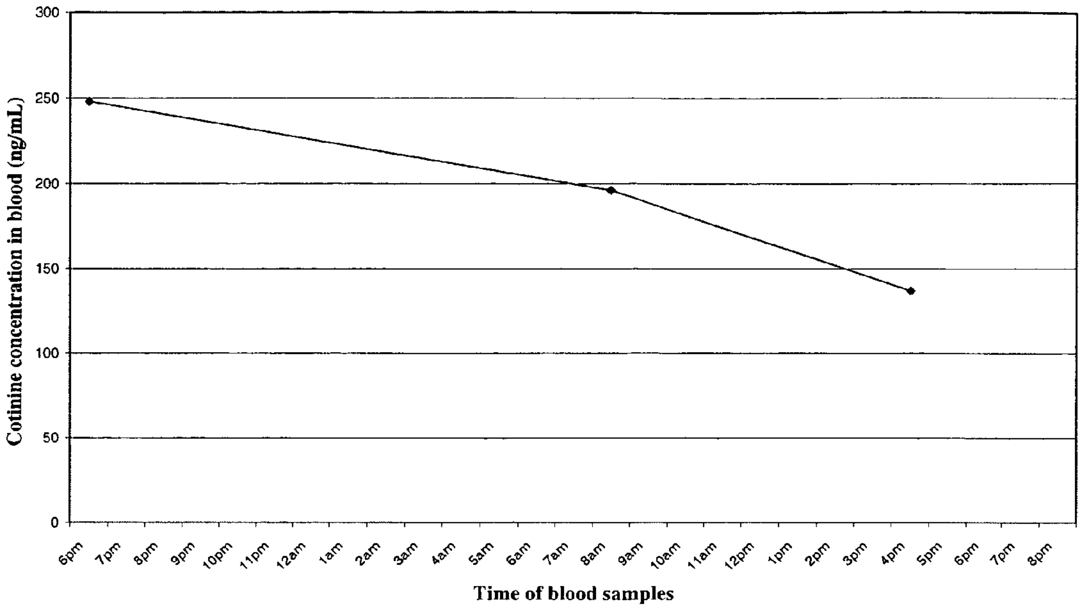
FIG. 4 is a graph showing the average blood cotinine concentration in subjects over the course of Experiment Two.
Figure 5:
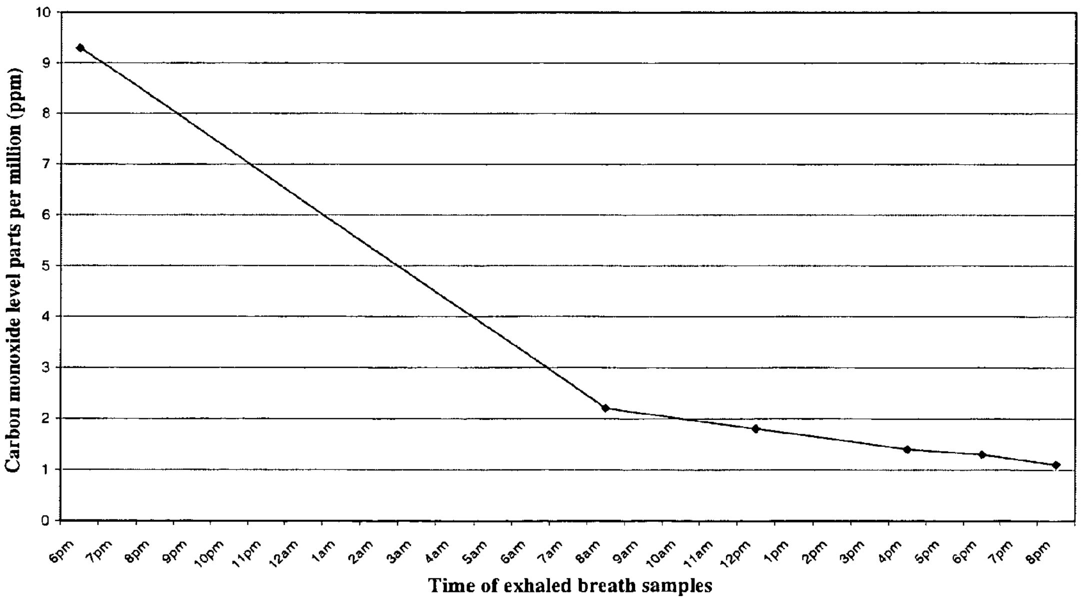
FIG. 5 is a graph showing the average concentration of CO in exhaled breath in subjects over the course of Experiment Two.

Day 2—6 pm
- Breathe into an apparatus used to collect and measure the CO in exhaled breath
- Complete the QSU-Brief Questionnaire and VAS
- Vital Signs control by a nurse Day 2—8 pm
- Breathe into an apparatus used to collect and measure the CO in exhaled breath
- Complete the QSU-Brief Questionnaire and VAS
- Vital Signs control by a nurse Study Results FIG. 4 shows a reduction in the average blood cotinine concentration in subjects over the course of the study, while FIG. 5 shows a reduction in the average concentration of CO in exhaled breath of subjects. These results confirm the subjects were not smoking during the course of the study.

When a subject does not smoke and does not receive treatment, his craving increases. The method of the invention reduces his craving or reduces his craving increase during the treatment period. This effect is clearly shown in the QSU and VAS curves (FIGS. 6 and 7) where not only the group as an average has not increased its craving but decreased its craving compared to the starting point. The time of each electro-acupuncture session is indicated by arrows in FIGS. 6 and 7.

Figure 6:
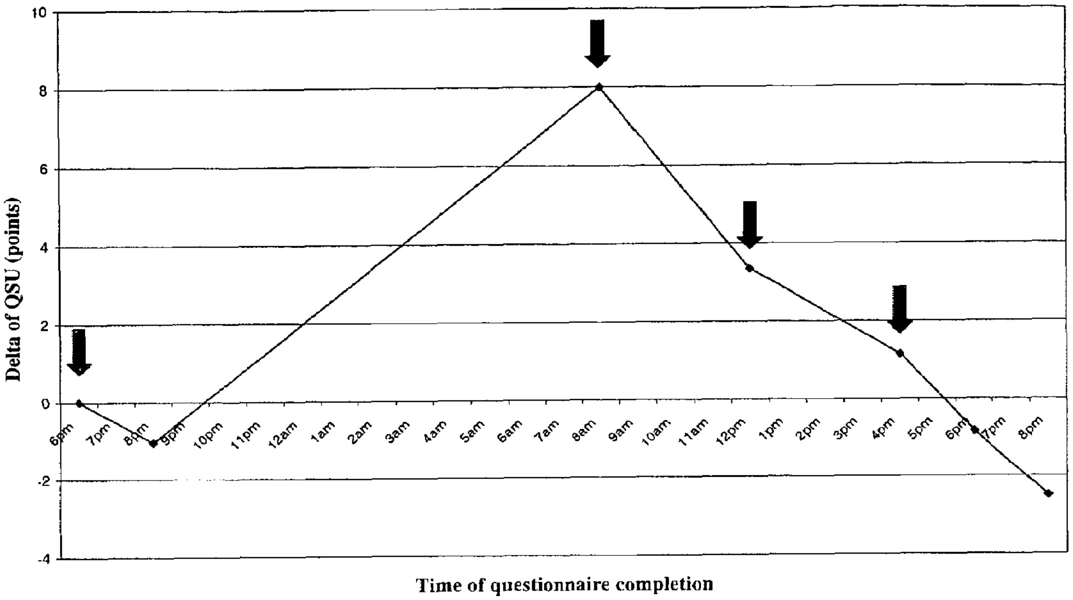
FIG. 6 is a graph showing the average change in QSU score over the course of Experiment Two. Arrows indicate the time of each electro-acupuncture session.
Figure 7:
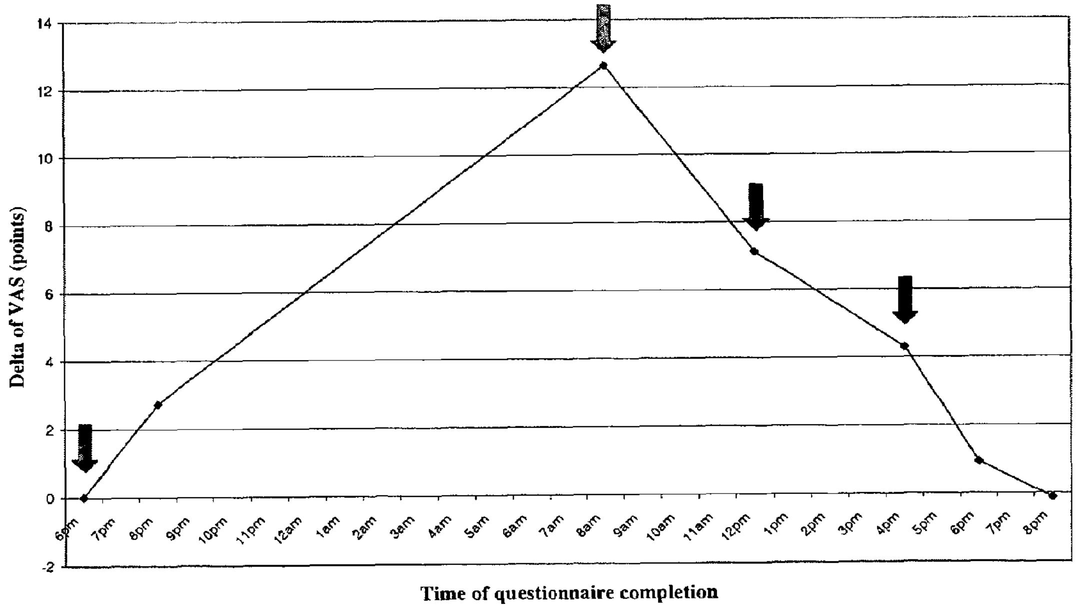
FIG. 7 is a graph showing the average change in VAS score over the course of Experiment Two. Arrows indicate the time of each electro-acupuncture session

After one day without smoking (as assessed by the compliance measures), the mean of the tobacco craving QSU scores within the two groups treated with the method of the invention has decreased, as shown in FIG. 6. In contrast, without any treatment craving would be expected to increase following smoking cessation. Similar results are observed with mean VAS score, as shown in FIG. 7.

We also observed a dose efficacy effect when comparing the group receiving 10 mA and the group receiving 5 mA stimulation when analyzing the strength of the response by absolute drop along the QSU score, as illustrated in Table 1.

TABLE 1

Percentage of Subjects in Which QSU Score Decreased

| QSU change | 10 mA (n = 20) | 5 mA (n = 20) |
|---|---|---|
| Decease >20 points (n) | 25% (5) | 10% (2) |
| Decrease >10 points* (n) | 50% (10) | 25% (5) |

*Cumulative

INDUSTRIAL APPLICATION

The method of the invention may be employed by individuals to help them abstain from or completely avoid smoking.

Where in the foregoing description reference has been made to elements or integers having known equivalents, then such equivalents are included as if they were individually set forth.

Although the invention has been described by way of example and with reference to particular embodiments, it is to be understood that modifications and/or improvements may be made without departing from the scope or spirit of the invention.

In addition, where features or aspects of the invention are described in terms of Markush groups, those skilled in the art will recognise that the invention is also thereby described in terms of any individual member or subgroup of members of the Markush group.

REFERENCES

Ausfeld-Hafter B, Marti F, Hoffmann S. Smoking cessation with ear acupuncture. Descriptive study on subjects after a smoking cessation treatment with ear acupuncture. Forschende Komplementarmedizin und Klassische Naturheilkunde 2004; 11(1):8-13.

Bier I. D, Wilson J, Studt P, Shakleton M. Auricular acupuncture, education, and smoking cessation: a randomized, sham-controlled trial. American Journal of Public Health 2002; 92(10): 1642-7.

Borchgrevink C. F. Research in alternative medicine. What is documented, and what is documentation? Tidsskrift for Den Norske Laegeforening 1997; 117(17):2469-73.

Clavel-Chapelon F, Paoletti C, Benhamou S. A randomised 2×2 factorial design to evaluate different smoking cessation methods. Revue d Epidemiologie et de Sante Publique 1992; 40(3): 187-90.

Clavel-Chapelon F, Paoletti C, Benhamou S. Smoking cessation rates 4 years after treatment by nicotine gum and acupuncture. Preventive Medicine 1997; 26(1):25-8.

Cottraux J, Schbath J, Messy P, Mollard E, Juenet C, Collet L. Predictive value of MMPI scales on smoking cessation programs outcomes. Acta Psychiatrica Belgica 1986; 86(4):463-9.

Cox L. S., Tiffany S. T, Christen A. G. Evaluation of the brief questionnaire of smoking urges (QSU-brief) in laboratory and clinical settings. Nicotine Tob Res. February 2001; 3(1):3-6.

Ernst E. Acupuncture-how effective is it really? Fortschritte der Medizin 1998; 116(1-2):20-6.

Fuller J. A. Smoking withdrawal and acupuncture. Medical Journal of Australia 1982; 1(1):28-9, 1982

Garrison M. M, Christakis D. A, Ebel B. E, Wiehe S. E, Rivara F. P. Smoking cessation interventions for adolescents: a systematic review. American Journal of Preventive Medicine 2003; 25(4):363-7.

Grau A. I., Prous J. R. Nicotine Addiction—Excecutive Summary. Drugs Today (Barc), 2005; June; 41(6):419-25.

Haustein K. O. Institute for Nicotine Research and Smoking Cessation, Erfurt, Germany. Pharmacotherapy of nicotine dependence. International Journal of Clinical Pharmacology & Therapeutics 2000; 38(6):273-90.

He D, Berg J. E, Hostmark A. T. Effects of Acupuncture on Smoking Cessation or Reduction for Motivated Smokers. Preventive Medicine 1997; 26:208-214.

He D, Medbo J. I, Hostmark A T. Effect of acupuncture on smoking cessation or reduction: an 8-month and 5-year follow-up study. Preventive Medicine 2001; 33(5):364-72.

Kelley M. J and McCrory D. C Prevention of lung cancer: summary of published evidence. Chest 2003; 123(1 Suppl):50S-59S.

Lando H. A. Smoking cessation products and programs. Alaska Medicine 1996; 38(2):65-68.

Law M. and Tang J. L. An analysis of the effectiveness of interventions intended to help people stop smoking. Archives of Internal Medicine 1995; 155(18):1933-41.

Linde K, Vickers A, Hondras M, ter Riet G, Thormahlen J, Berman B, Melchart D. Systematic reviews of complementary therapies—an annotated bibliography. Part 1: acupuncture. BMC Complementary & Alternative Medicine 2001; 1(1):3.

Margolin A, Avants S. K, Holford T. R. Interpreting conflicting findings from clinical trials of auricular acupuncture for cocaine addiction: does treatment context influence outcome? Journal of Alternative & Complementary Medicine 2002; 8(2):111-21.

Mohit A. A brief overview of Drug Abuse and Guiding principles for building programs for reducing demand and harm related to the abuse of drug. The First Consultation of Regional Advisory Panel on the Impact of Drug Abuse (RAPID) Cairo, Egypt, Sep. 23-26 2002.

Tiffany S. T., Drobes D. J. The development and initial validation of a questionnaire on smoking urges. British Journal of Addiction November 1991; 86(11):1467-76.

Waite N. R and Clough J. B. A single-blind, placebo-controlled trial of a simple acupuncture treatment in the cessation of smoking. British Journal of General Practice 1998; 48(433):1487-90.

White A. R, Resch K. L, Ernst E. Randomized trial of acupuncture for nicotine withdrawal symptoms. Archives of Internal Medicine 1998; 158(20):2251-5.

White A. R, Resch K. L, Ernst E. A meta-analysis of acupuncture techniques for smoking cessation. Tobacco Control 1999; 8(4):393-7.

White A. R, Rampes H, Ernst E. Acupuncture for smoking cessation. [update of Cochrane Database Syst Rev. 2000; (2):CD000009. Cochrane Database of Systematic Reviews 2002; (2):CD000009.

Willemsen M. C, Wagena E. J, van Schayck C. P. The efficacy of smoking cessation methods available in the Netherlands: a systematic review based on Cochrane data. Nederlands Tijdschrift voor Geneeskunde 2003; 147(19):922-7.

Yiming C, Changxin Z, Ung W. S, Lei Z, Kean L. S. Laser acupuncture for adolescent smokers—a randomized double-blind controlled trial. American Journal of Chinese Medicine 2000; 28(3-4):443-9.

What I claim is:

1. A method of reducing a desire to smoke in a subject in need thereof comprising:

placing at least a first electrode and a second electrode substantially in or on the subject in a vicinity of at least one acupuncture point selected from two or more acupuncture points in or on the subect's arms or hands, wherein the placing includes placing at least the first electrode and the second electrode in or on opposite sides of an arm or hand of the subject in which the at least one selected acupuncture point is located; and applying an electrical current to the subject in the vicinity of the at least one selected acupuncture points, wherein said electrical current is alternated between at least two frequencies every 1, 2, 3, 4 or 5 seconds, and wherein said electrical current is applied through at least the first electrode and the second electrode.

2. A method as claimed in claim 1 wherein said at least one acupuncture point is selected from:

a Hegu acupuncture point, a point in or on a side of one of the subject's hands opposite to the Hegu acupuncture point, the Nei guan acupuncture point, and the Wai guan acupuncture point.

3. A method as claimed in claim 2 wherein the two or more acupuncture points comprises at least one of two, three and four selected acupuncture points and wherein said electrical current is applied in the vicinity of two or more acupuncture points.

4. A method as claimed in claim 2 wherein the at least one acupuncture point selected from two or more acupuncture points in or on the subjects arms and hands comprises two, three, or four acupuncture points, and wherein applying said electrical current comprises applying said electrical current at or within about 0.5, 0.6, 0.7, 0.8, 0.9, 1 or 2 cm of the two, three or four selected acupuncture points.

5. A method as claimed in claim 2 wherein said electrical current is applied at a level equal to, greater than, or about two times a level equal to a pain threshold of the subject.

6. A method as claimed in claim 5 wherein said electrical current is at least about 1, 2, 4, 5, 6, 8, 10, 12, 14, 16, 18, 20, 22 or 24 mA.

7. A method as claimed in claim 6 wherein said electrical current is applied at a frequency of about 1 Hz to about 120 Hz, or about 2 Hz to about 100 Hz.

8. A method as claimed in claim 2 wherein said method is carried out according to a regime comprising:

a) an initial period, and b) a weaning period.

9. A method as claimed in claim 8 wherein said initial period is about 2 weeks to about 8 weeks in duration.

10. A method as claimed in claim 8 wherein during said initial period the method is carried out two, three, four or five times daily.

11. A method as claimed in claim 8 wherein said weaning period is about two weeks to about 12 weeks in duration.

12. A method as claimed in claim 11 wherein during said weaning period the method is carried out one or two times daily.

13. A method as claimed in claim 1 wherein the first electrode and the second electrode comprise needle electrodes or skin contact electrodes.

14. A method as claimed in claim 1 wherein said first electrode and said second electrode comprise skin contact electrodes and the placing includes placing at least the first electrode and the second electrode on a first and second skin surfaces, respectively, on opposite sides of an arm or hand of the subject in which the at least one selected acupuncture point is located, surface adjacent the selected acupuncture point and a second skin contact electrode on a second skin surface adjacent the selected acupuncture point.

15. A method as claimed in claim 1 wherein the electrical current is app lied in the vicinity of the at least one selected acupuncture point to stimulate one or more of the at least one selected acupuncture point, a nerve, subcutaneous tissue, muscle fibers and a biological system.

16. A method as claimed in claim 1 wherein said frequency of the electrical current is alternated from a frequency of about 1, 2, 3, 4, 5, 6, 7, 8, 9 or 10 Hz to a frequency of about 30, 40, 50, 60, 70, 80, 90, 100, 110 or 120 Hz.

17. A method as claimed in claim 1 wherein said electrical current is app lied to at least the first electrode and the second electrode simultaneously.

18. A method as claimed in claim 1 wherein said electrical current is applied through at least the first electrode and the second electrode via an electro-acupuncture device such that at least the first electrode and the second electrode receive said electrical current from the electro-acupuncture device.

19. A method as claimed in claim 18 wherein said electro-acupuncture device has at least a first channel and a second channel which can independently provide an electrical current.

20. A method as claimed in claim 19 wherein each said channel is connected to one or more electrodes.

21. A method as claimed in claim 20 wherein said first channel provides a first set of conditions and said second channel provides a second set of conditions.

22. A method of aiding smoking cessation in a subject in need thereof comprising:

placing at least a first electrode and a second electrode substantially in or on the subject in a vicinity of at least one acupuncture point selected from two or more acupuncture points in or on the subject's arms or hands, wherein the placing includes placing at least the first electrode and the second electrode in or on opposite sides of an arm or hand of the subject in which the at least one selected acupuncture point is located; and applying an electrical current to the subject in the vicinity of the at least one selected acupuncture points, wherein said electrical current is alternated between at least two frequencies every 1, 2, 3, 4 or 5 seconds, and wherein said electrical current is applied through at least a the first electrode and the second electrode.

23. A method of alleviating symptoms of nicotine withdrawal in a subject in need thereof comprising:

placing at least a first electrode and a second electrode substantially in or on the subject in a vicinity of at least one acupuncture point selected from two or more acupuncture points in or on the subject's arms or hands, wherein the placing includes placing at least the first electrode and the second electrode in or on opposite sides of an arm or hand of the subject in which the at least one selected acupuncture point is located; and applying an electrical current to the subject in the vicinity of the at least one selected acupuncture points, wherein said electrical current is alternated between at least two frequencies and said frequency is alternated every 1, 2, 3, 4 or 5 seconds, and wherein said electrical current is applied through at least the first electrode and the second electrode.

24. A method of alleviating symptoms of craving resulting from nicotine addiction in a subject in need thereof comprising:

placing at least a first electrode and a second electrode substantially in or on the subject in a vicinity of at least one acupuncture point selected from two or more acupuncture points in or on the subject's arms or hands, wherein the placing includes placing at least the first electrode and the second electrode in or on opposite sides of an arm or hand of the subject in which the at least one selected acupuncture point is located; and applying an electrical current to the subject in the vicinity of the at least one selected acupuncture points, wherein said electrical current is alternated between at least two frequencies every 1, 2, 3, 4 or 5 seconds, and wherein said electrical current is applied through at least the first electrode and the second electrode.

25. A method of reducing or alleviating nicotine craving in a subject in need thereof comprising placing at least a first electrode and a second electrode substantially in or on the subject in a vicinity of at least one acupuncture point selected from two or more acupuncture points in or on the subject's arms or hands, wherein the placing includes placing at least the first electrode and the second electrode in or on opposite sides of an arm or hand of the subject in which the at least one selected acupuncture point is located; and applying an electrical current to the subject in the vicinity of the at least one selected acupuncture points, wherein said electrical current is alternated between at least two frequencies every 1, 2, 3, 4 or 5 seconds, and wherein said electrical current is applied through at least the first electrode and the second electrode.

26. A method of treating nicotine addiction in a subject in need thereof comprising:

placing at least a first electrode and a second electrode substantially in or on the subject in a vicinity of at least one acupuncture point selected from two or more acupuncture points in or on the subject's arms or hands, wherein the placing includes placing at least the first electrode and the second electrode in or on opposite sides of an arm or hand of the subject in which the at least one selected acupuncture point is located; and applying an electrical current to the subject in the vicinity of the at least one selected acupuncture points, wherein said electrical current is alternated between at least two frequencies every 1, 2, 3, 4 or 5 seconds, and wherein said electrical current is applied through at least the first electrode and the second electrode.

* * * * *

UNITED STATES PATENT AND TRADEMARK OFFICE

CERTIFICATE OF CORRECTION

PATENT NO. : 7,689,287 B2
APPLICATION NO. : 11/244011
DATED : March 30, 2010
INVENTOR(S) : Han It is certified that error appears in the above-identified patent and that said Letters Patent is hereby corrected as shown below:

Column 1, Line 50 – Replace “researches” with --researchers--.

Column 4, Line 38 – Replace “be the broadly” with --be read broadly--.

Column 8, Line 17 – Replace “patent’s” with --patient’s--.

Column 8, Line 57 – Replace “patent” with --patient--.

Column 11, Line 43 – Replace “12 am” with --12 pm--.

Column 14, Line 13 – Replace “CD000009.” with --CD000009.]--.

Column 15, Line 30 – Replace “app lied” with --applied--.

Column 15, Line 38 – Replace “app lied” with --applied--.

Column 16, Line 1 – Replace “least a the” with --least the--.

Signed and Sealed this

Twentieth Day of July, 2010

David J. Kappos

*Director of the United States Patent and Trademark Office*